US012245749B2

(12) United States Patent
Jia et al.

(10) Patent No.: US 12,245,749 B2
(45) Date of Patent: Mar. 11, 2025

(54) ENDOSCOPIC THREE-DIMENSIONAL IMAGING SYSTEMS AND METHODS

(71) Applicant: Georgia Tech Research Corporation, Atlanta, GA (US)

(72) Inventors: Shu Jia, Atlanta, GA (US); Changliang Guo, Atlanta, GA (US); Tara Urner, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 471 days.

(21) Appl. No.: 17/762,767

(22) PCT Filed: Oct. 5, 2020

(86) PCT No.: PCT/US2020/054262
§ 371 (c)(1),
(2) Date: Mar. 23, 2022

(87) PCT Pub. No.: WO2021/067934
PCT Pub. Date: Apr. 8, 2021

(65) Prior Publication Data
US 2022/0345831 A1 Oct. 27, 2022
US 2023/0284883 A9 Sep. 14, 2023

Related U.S. Application Data

(60) Provisional application No. 62/909,902, filed on Oct. 3, 2019.

(51) Int. Cl.
*A61B 1/00* (2006.01)
*A61B 1/07* (2006.01)
*H04R 25/00* (2006.01)

(52) U.S. Cl.
CPC ...... *A61B 1/00193* (2013.01); *A61B 1/00009* (2013.01); *A61B 1/00163* (2013.01);
(Continued)

(58) Field of Classification Search
CPC ............ A61B 1/00009; A61B 1/00163; A61B 1/00193; A61B 1/00194; A61B 1/07
See application file for complete search history.

(56) References Cited

U.S. PATENT DOCUMENTS 5,459,605 A * 10/1995 Kempf .................. A61B 1/055
359/476
5,513,271 A * 4/1996 Rao ...................... G06V 30/412
382/113
(Continued)

OTHER PUBLICATIONS

International Search Report and Written Opinion from Application No. PCT/US2020/054262 dated Jan. 12, 2021.
(Continued)

*Primary Examiner* — Aaron B Fairchild
(74) *Attorney, Agent, or Firm* — Troutman Pepper Locke LLP; Ryan A. Schneider; Stephanie J. Remy

(57) ABSTRACT

Disclosed is an endoscopic imaging system, comprising a camera, a plurality of GRIN lenses, a processor, and a memory. Each GRIN optical lens can have a first end configured to be inserted into a cavity of a subject and receive light reflected from a point of interest in the cavity of the patient and a second end configured to transmit the light to the camera. The light can be representative of a distinct image of a perspective view of the point of interest relative to the respective GRIN optical lens. The system can: generate image data corresponding to the light received from each of the plurality of GRIN optical lenses; deconvolve the image data to generate deconvolved image data representative of the distinct images; and generate, using the deconvolved image data, 3D image data representative of a 3D image of the point of interest.

27 Claims, 11 Drawing Sheets

(52) U.S. Cl.
CPC ............ *A61B 1/00194* (2022.02); *A61B 1/07* (2013.01); *H04R 25/30* (2013.01)

(56) References Cited

U.S. PATENT DOCUMENTS

| | | |
|---|---|---|
| 2003/0076571 A1 | 4/2003 | MacAulay et al. |
| 2010/0049002 A1* | 2/2010 | Feldman ............ G01B 9/02091 359/207.6 |
| 2018/0234600 A1 | 8/2018 | Zeien |

OTHER PUBLICATIONS

Matthias, et al., "A 3D Measuring Endoscope for Hand-Guided Operation," Measurement and Technology Aug. 1, 2018.
Guo, et al., "3D Light-Field Endoscopic Imaging Using a GRIN Lens Array," Applied Physics Letters Mar. 12, 2020 116, 101105-1-101105-5.

* cited by examiner

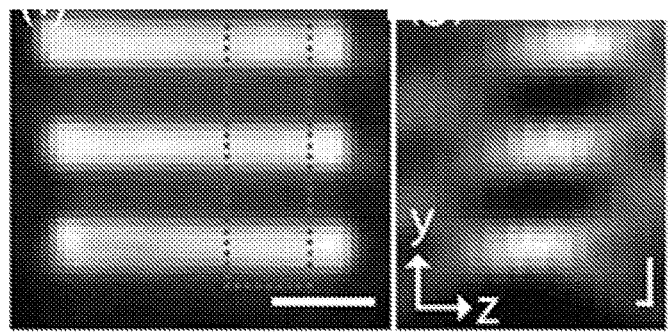
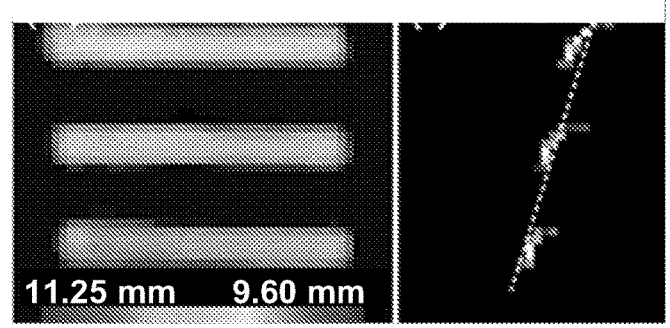
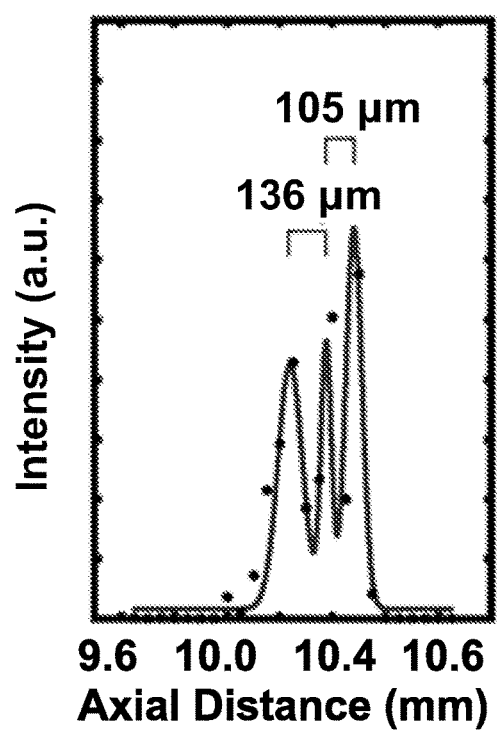

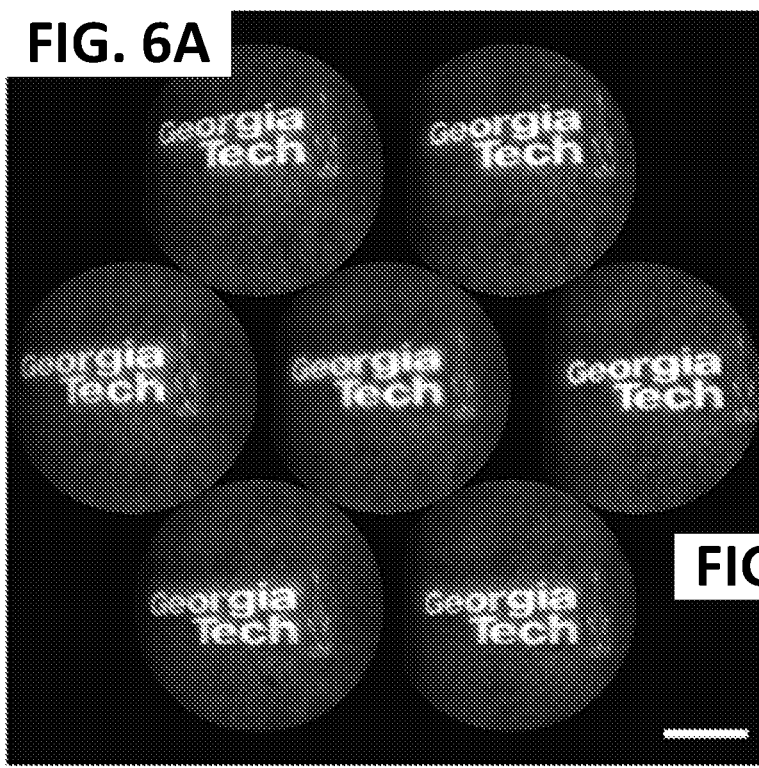
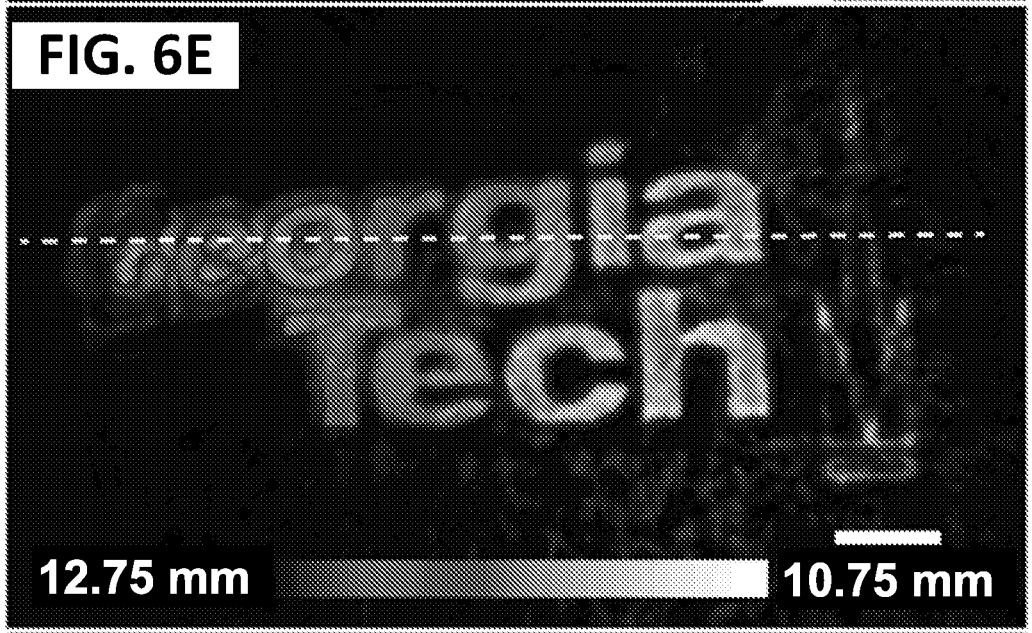
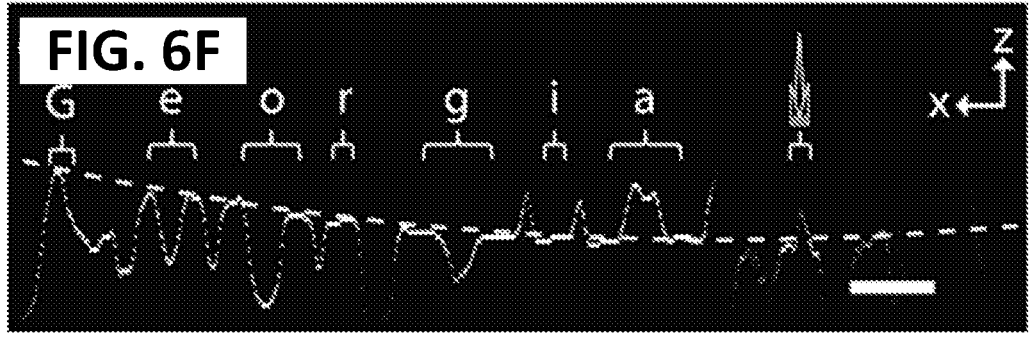
FIG. 6A  FIG. 6B  z = 12.75 mm  FIG. 6C  z = 11.40 mm  FIG. 6D  FIG. 6E  12.75 mm  10.75 mm  FIG. 6F

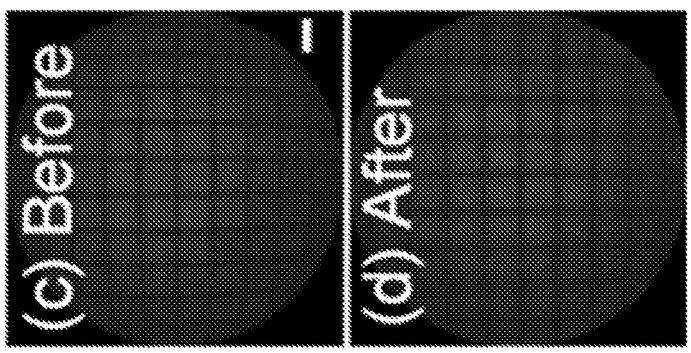
FIG. 7A
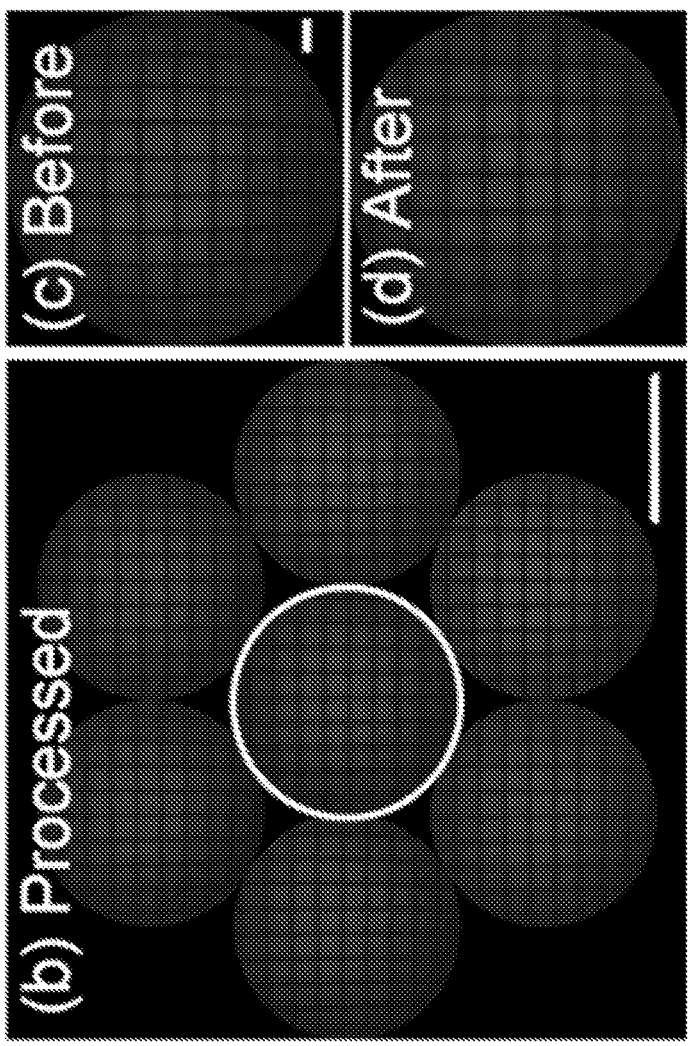
FIG. 7B
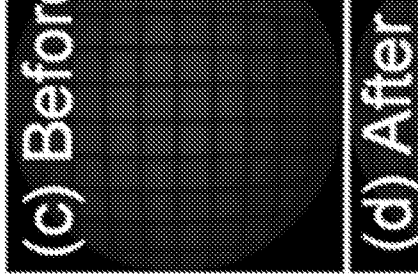
FIG. 7C
FIG. 7D

ENDOSCOPIC THREE-DIMENSIONAL IMAGING SYSTEMS AND METHODS

CROSS-REFERENCE TO RELATED APPLICATIONS

This application claims the benefit of U.S. Provisional Application Ser. No. 62/909,902, filed on 3 Oct. 2019, which is incorporated herein by reference in its entirety as if fully set forth below.

FIELD OF THE DISCLOSURE

The various embodiments of the present disclosure relate generally to imaging systems methods, and more particularly to endoscopic three-dimensional systems and methods.

BACKGROUND

Optical endoscopy has emerged as an indispensable clinical tool, enabling minimally invasive diagnostics, surgeries and therapeutics, and has greatly reduced the risk of infection, patient recovery time, and medical cost. Today, most clinical endoscopy systems provide only a two-dimensional (2D) projection of complex three-dimensional (3D) structures, thereby limiting effective anatomic landmark recognition. This is particularly salient for clinical cases that require high precision in all three dimensions such as pathologies with significant in-depth extension, vascular encasement, or dense tumor structures. In fact, without a quantitative 3D map of the tissue anatomy, surgeons and surgical robotic systems may lack the full spatial awareness necessary to maximize efficient, safe navigation.

The recent development of 3D endoscopy offers visual parallax of the surgical field mediated by specialized eyeglasses in order to provide stereoscopic vision and depth perception and, as a result, enhance the understanding of anatomy, compared to the 2D endoscopy systems. However, despite the promise of 3D imaging to improve surgery and surgical training, the current stereoscopic, two-display scheme realizes only the illusion of the 3D object and has been restricted by several practical considerations in instrumentation complexity, data rendering and operating maneuverability, as well as the clinical quantitative measures, compared with the 2D counterparts. As such, the advancement of optical strategies for 3D endoscopic imaging is still highly demanded.

To address the need, several conventional optical approaches to quantitative 3D endoscopic imaging have been proposed in recent years, including methods using stereoscopic optics, spatially or temporally modulated light, scanning using fiber optics, liquid crystal or electro-wetting lenses, or holography. Notably, amongst the existing works, light-field techniques have rapidly emerged as a promising candidate for 3D imaging due to their high scalability and volumetric imaging capability. These techniques include approaches that implement a light-field module downstream from traditional endoscopic optics or methods that replace the original entrance optics with a variety of lens or fiber arrays. In particular, the former scheme retains the primary spatial characteristics and instrumentation of 2D endoscopy systems, while the latter maximizes the collection of angular information, enhancing the axial sectioning capability and resolution. However, the optimum scenario for light-field imaging requires dense sampling of both the spatial and the angular information of optical signals. To this end, a new optical design and computational framework remains highly desired for high-resolution, volumetric endoscopic imaging.

BRIEF SUMMARY

The present disclosure relates to endoscopic imaging systems and methods. An exemplary embodiment of the present disclosure provides an endoscopic imaging system comprising a camera, a plurality of gradient-index (GRIN) optical lenses, a processor, and a memory. Each of the GRIN optical lenses can have a first end and a second end. The first end can be configured to be inserted into a cavity of a subject and receive light reflected from a point of interest in the cavity of the patient. The light can be representative of a distinct image of a distinct perspective view of the point of interest relative to the respective GRIN optical lens. The second end can be configured to transmit the light to the camera. The memory can comprise instructions that, when executed by the processor, cause the processor to: generate image data corresponding to the light received from each of the plurality of GRIN optical lenses; deconvolve the image data to generate deconvolved image data representative of the distinct images of the distinct perspective view of the point of interest relative to the respective GRIN optical lenses; and generate, using the deconvolved image data, three-dimensional (3D) image data representative of a 3D image of the point of interest.

In any of the embodiments disclosed herein, the endoscopic imaging system can further comprise a relay lens system comprising one or more relay lenses. The relay lens system can be configured to receive the light from the second ends of the plurality of GRIN optical lenses and transfer the light to the camera.

In any of the embodiments disclosed herein, the plurality of GRIN optical lenses can be arranged substantially parallel to one another.

In any of the embodiments disclosed herein, the endoscopic imaging system can further comprise a tube. The plurality of GRIN lenses can be located, at least partially, within the tube.

In any of the embodiments disclosed herein, the tube can be in the shape an of elongated cylinder.

In any of the embodiments disclosed herein, the plurality of GRIN optical lenses can comprise three GRIN optical lenses.

In any of the embodiments disclosed herein, the GRIN optical lenses can be arranged such that a cross-section along a length of the lenses forms a triangular shape.

In any of the embodiments disclosed herein, the plurality of GRIN optical lenses can comprise seven GRIN optical lenses.

In any of the embodiments disclosed herein, the GRIN optical lenses can be arranged such that a cross-section along a length of the lenses forms a hexagonal shape.

In any of the embodiments disclosed herein, the endoscopic imaging system can further comprise a light source configured to illuminate the point of interest.

In any of the embodiments disclosed herein, the light source can comprise one or more optical fibers.

In any of the embodiments disclosed herein, each of the one or more optical fibers can comprises a first end and a second end. The first ends of the one or more optical fibers can be positioned adjacent the first ends of the plurality of GRIN optical lenses.

In any of the embodiments disclosed herein, the endoscopic imaging system can further comprise a body configured to support the camera and the plurality of GRIN optical lenses. The body can comprise an aperture. The second ends of the one or more optical fibers can be positioned adjacent the aperture, such that light from an area outside the body can pass through the aperture to the second ends of the one or more optical fibers.

In any of the embodiments disclosed herein, the memory can further comprise instructions, that when executed by the processor, cause the processor to generate an output signal to a display to cause the display to display the 3D image of the point of interest.

In any of the embodiments disclosed herein, the memory cam further comprise instructions, that when executed by the processor, cause the processor to deconvolve the image data to generate deconvolved image data by applying a Richardson-Lucy deconvolution method.

In any of the embodiments disclosed herein, the memory cam further comprise instructions, that when executed by the processor, cause the processor to deconvolve the image data to generate deconvolved image data by applying a point spread function associated with the endoscopic imaging system.

Another embodiment of the present disclosure provides a method of generating a 3D image of a point of interest in a cavity of a subject. The method cam comprise: providing an endoscopic imaging system; inserting the first ends of the plurality of GRIN optical lenses into the cavity of the subject; illuminating the point of interest; receiving, with each of the first ends of the plurality of GRIN optical lenses, light reflected from the point of interest, the light representative of a distinct image of a distinct perspective view of the point of interest relative to the respective GRIN optical lens; transmitting the light from the second ends of the plurality of GRIN optical lenses to the camera; generating image data corresponding to the light received from each of the plurality of GRIN optical lenses; deconvolving the image data to generate deconvolved image data representative of the distinct images of the distinct perspective views of the point of interest relative to the respective GRIN optical lenses; and generating, using the deconvolved image data, 3D image data representative of a 3D image of the point of interest.

In any of the embodiments disclosed herein, transmitting the light from the second ends of the plurality of GRIN optical lenses to the camera comprises transmitting the light from the second ends of the plurality of GRIN optical lenses through the relay lens system and to the camera.

In any of the embodiments disclosed herein, inserting the first ends of the plurality of GRIN optical lenses into the cavity of the subject can comprise inserting at least a portion of the tube into the cavity of the subject.

In any of the embodiments disclosed herein, illuminating the point of interest can comprise directing light from the light source to the point of interest.

In any of the embodiments disclosed herein, illuminating the point of interest can comprise transferring light from an area outside of the body through the aperture to the second ends of the one or more optical fibers.

In any of the embodiments disclosed herein, the method can further comprise generating an output signal to a display to cause the display to display the 3D image of the point of interest.

In any of the embodiments disclosed herein, deconvolving the image data to generate deconvolved image data can comprise performing a Richardson-Lucy deconvolution method on the image data.

In any of the embodiments disclosed herein, generating the deconvolved image data cam comprise applying a point spread function associated with the endoscopic imaging system.

The method of claim 17, further comprising calibrating the endoscopic imaging system, wherein calibrating the endoscopic imaging system can comprise determining a point spread function for the endoscopic imaging system.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 5F provides the reconstruction of Group 2 Element 2 as shown in the boxed region of FIG. 5B. FIG. 5G provides a projected side-view image of the boxed region in FIG. 5F, showing the tilt of the structure. FIG. 5H provides the same region as in FIG. 5F after extracting the weighted maximum intensity. FIG. 5I shows a projected side-view image of the same region of FIG. 5H as in FIG. 5F, showing the surface information, in which the dotted line represents a linear fit to the pixels, exhibiting a slope of 46 degrees. FIG. 5J provides a profile of the axial projection of FIG. 5I, showing a Gaussian-fitted separations of 136 microns and 105 microns between the structures in the axial dimension.

FIG. 6A provides raw light-field images of a "Georgia Tech" logo on a conical tube. FIGS. 6B-C provide reconstructed focal stacks at the depths z=12.75 mm (FIG. 6B) and z=11.40 mm (FIG. 6C) from the GLA. FIG. 6D provides a cross-section profile along the line in FIG. 6C (i.e., the white line adjacent the "a" in "Georgia"). FIGS. 6E-F provide a 3D reconstructed image (FIG. 6E) and the cross-section view (FIG. 6F) along the dashed line in FIG. 6E. The reconstructed logo features agree well with the curved surface of the conical tube, outlined by the dashed curve in FIG. 6F.

FIG. 7A provides raw elemental images, showing distorted grid image from seven GRIN lenses. FIG. 7B provides the corresponding corrected and condensed elemental images after barrel distortion correction and removal of blank regions between them. FIGS. 7C-D provide zoomed-in images of the center elemental images before (FIG. 7C) and after (FIG. 7D) correction. The scale bars in FIGS. 7A-B are 1 mm. The scale bars in FIG. 7C is 150 microns.

In FIG. 8A, the working distance of the GRIN lens is denoted by s and the focal length by f. The image of the object is denoted as h' and the principal planes of the GRIN lens are H and H'.

DETAILED DESCRIPTION

To facilitate an understanding of the principles and features of the present invention, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

The present disclosure relates to endoscopic imaging systems and methods. In particular, various embodiments of the present disclosure provide light-field endoscopic imaging systems which can achieve volumetric recording and reconstruction using an array of GRIN lenses. The optical scheme can addresses 3D endoscopic imaging through two main considerations. First, GRIN lenses can be utilized to take advantages of their small diameters, long relay lengths, and high numerical aperture (NA). Thus, the use of GRIN lenses can provide consistent spatial measures as in many 2D endoscopic systems. Second, because of their compact size in comparison with compound objective lenses, GRIN lenses can allow for a practical array integration at the entrance optics, while extensively capturing the angular information used for 3D reconstruction. Second, from a computational standpoint, unlike conventional systems that retrieve the volumetric information based on ray optics, embodiments of the present disclosure can employ a wave-optics model and hybrid point spread function (PSF) for a high-resolution reconstruction of the full light field.

As shown in FIGS. 1A-B and 2A-B, an exemplary embodiment of the present disclosure provides an endoscopic imaging system. The system comprises a camera 105, a plurality of gradient-index (GRIN) optical lenses 110, a processor (not shown), and a memory (not shown). The camera 105 can be many different cameras known in the art. In an exemplary embodiment, the camera 105 is a digital camera, such as a CMOS camera.

Figure 1A:
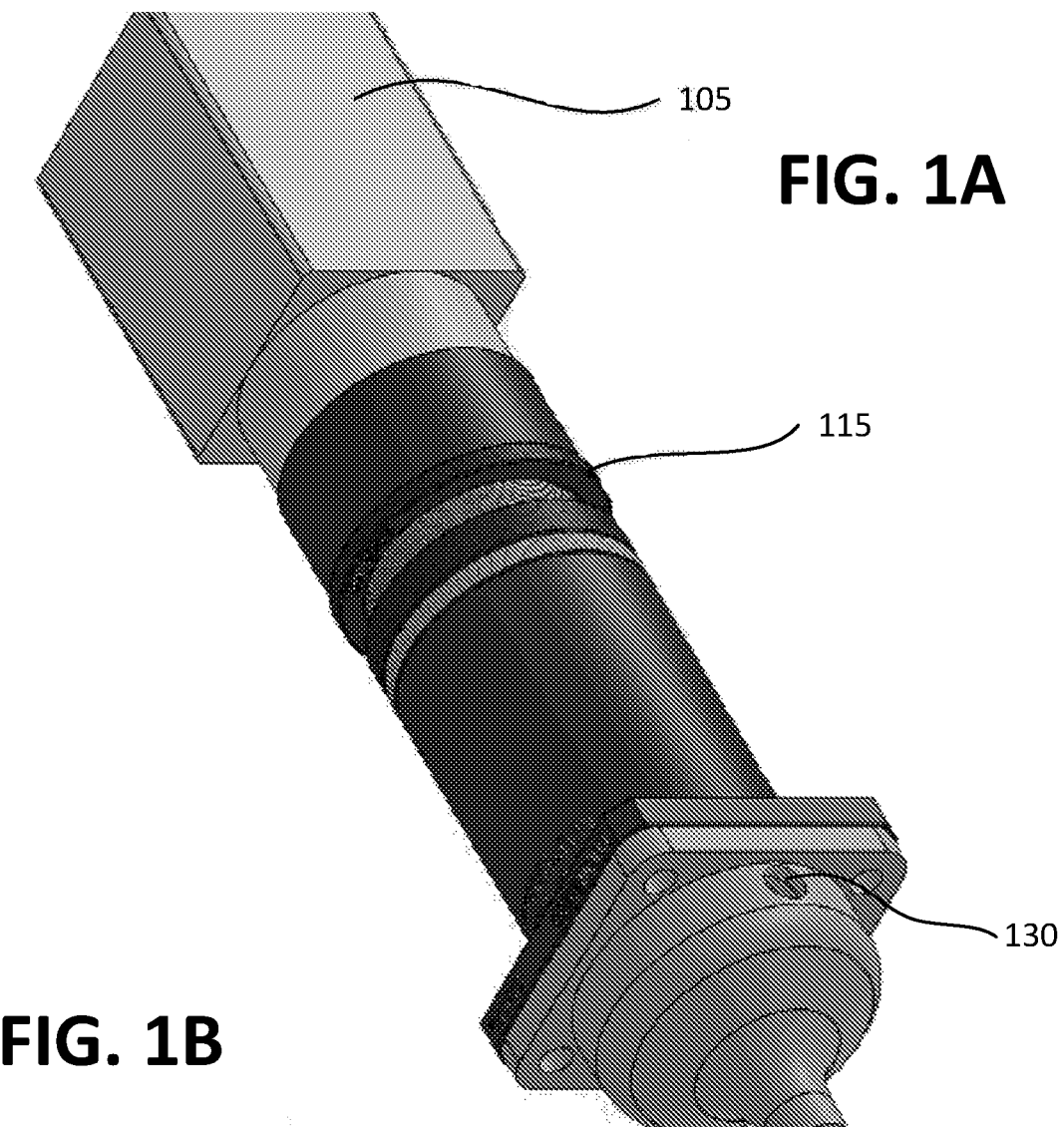
FIG. 1A provides a perspective view of an endoscopic imaging system, in accordance with an embodiment of the disclosure.
Figure 2A:
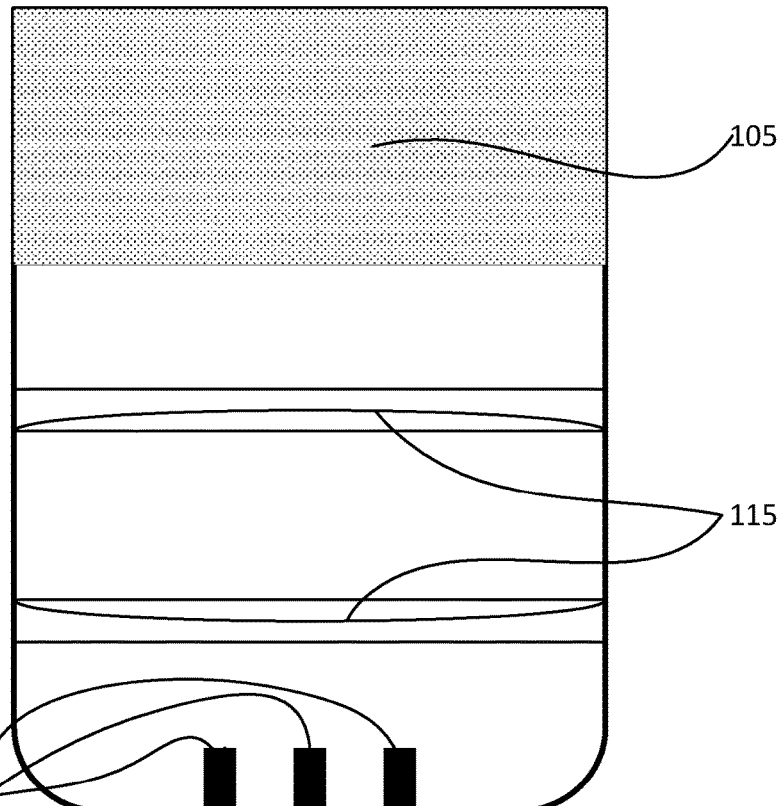
FIG. 2A provides a schematic of an endoscopic imaging system, in accordance with an embodiment of the disclosure.

The GRIN lenses can be many different types of GRIN lenses known in the art. Each of the GRIN optical lenses 110 can have a first end 111 and a second end 112. The first end 111 can be configured to be inserted into a cavity of a subject and receive light reflected from a point of interest in the cavity of the patient. Thus, the first end 111 can be positioned proximate an end of the imaging system, as shown in FIG. 2A. The light can be representative of a distinct image of a distinct perspective view of the point of interest relative to the respective GRIN optical lens. In other words, each of the lenses 110 can be oriented such that they receive light reflected from the point of interest at a distinct angle, thus creating a distinct perspective view of the point of interest relative to the respective lens. Thus, light reflected from the point of interest is received by a first lens to create a first distinct image of a first perspective view of the point of interest, and light reflected from the point of interest is received by a second lends to create a second distinct image of a second perspective view (due to the different physical positions of the first and second lens) of the point of interest. Each lens can capture a slightly different perspective view of the point of interest, such that those distinct images of the distinct perspective views together can be used to form a three-dimensional image, as discussed below. The second end 112 can be configured to transmit the light to the camera 105. Thus, light passes from the point of interest, into the first ends 111 of the lens 110, through lens 110, out of the second ends 112, and to the camera 105. In some embodiments, as shown in FIGS. 1A and 2A, the endoscopic imaging system can further comprise a relay lens system comprising one or more relay lenses 115. The relay lens system can be configured to receive the light from the second ends 112 of the plurality of GRIN optical lenses 110 and transfer the light to the camera 105.

Figure 1B:
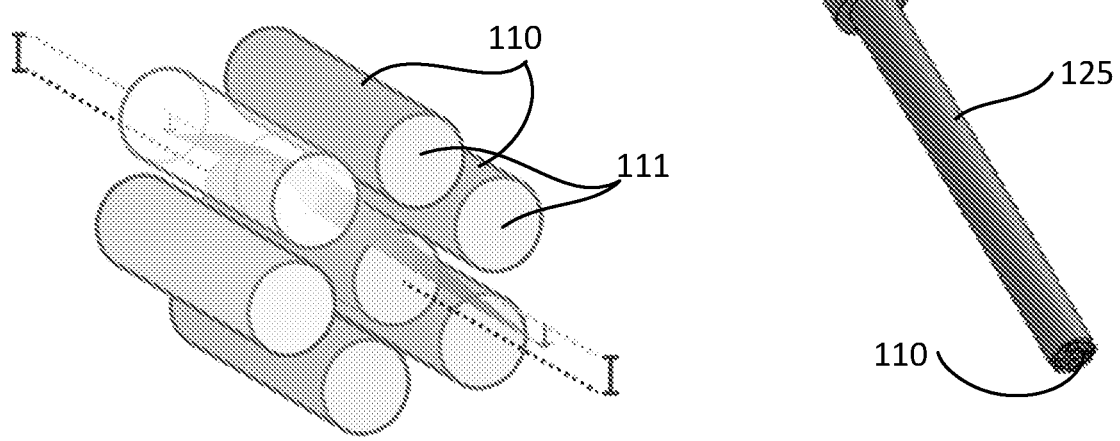
FIG. 1B provides a zoomed in view of a plurality of GRIN optical lenses shown in FIG. 1A, in accordance with an exemplary embodiment of the disclosure.
Figure 2B:
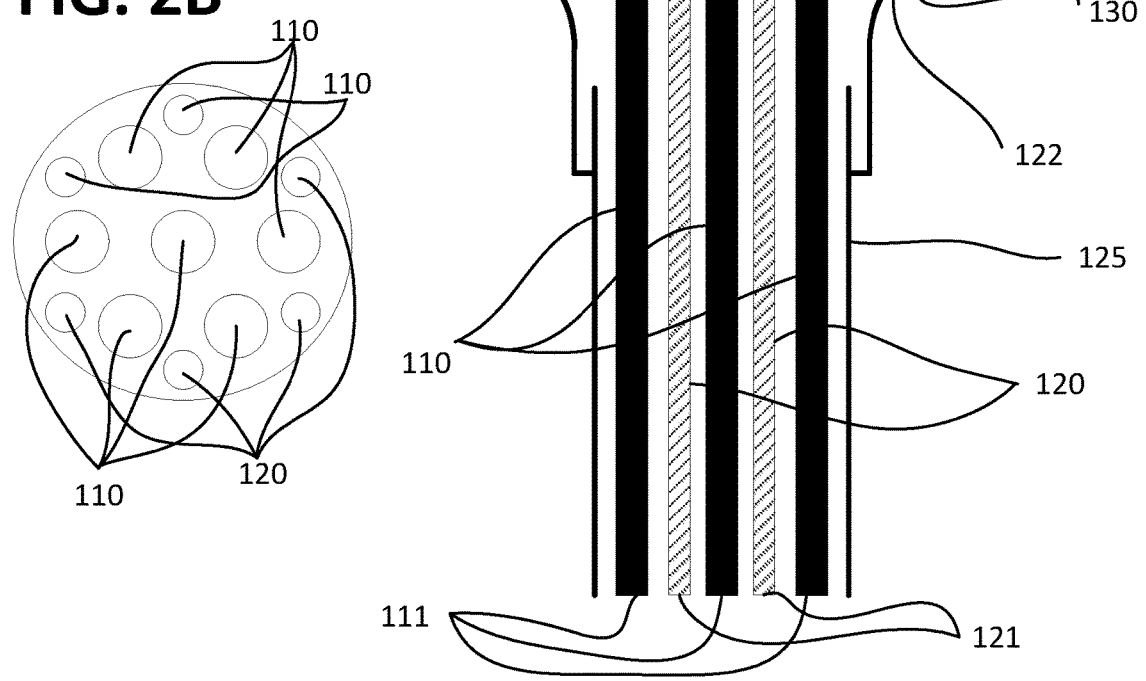
FIG. 2B provides a zoomed in view of a cross-section of a potion of the endoscopic imaging system shown in FIG. 2A proximate an end of the tube of the system.

The endoscopic imaging system can comprise many different numbers of lenses. For example, in some embodiments, the system comprises three lenses 110. In some embodiments, as shown in FIGS. 1B and 2B, the system can comprise seven lenses 110. Additionally, the lenses can be oriented any many different configurations. For example, the lenses can be oriented such that the cross-section of the lenses along their length is triangular shaped (particularly when three lenses are used) or hexagonally shaped (particularly when seven lenses are used). FIGS. 1B and 2B illustrate the use of seven lenses oriented to form a hexagonally-shaped cross section.

The GRIN lenses can have many different shapes. For example, in some embodiments, as shown in FIGS. 1B and 2A-B, the lenses 110 can by cylindrically shaped. The disclosure, however, is not so limited and should be construed to cover lenses 110 having other shapes. In some embodiments, the plurality of GRIN optical lenses can be arranged substantially parallel to one another, as shown in FIGS. 1B and 2A.

The endoscopic imaging system can further comprise a tube 125. As shown in FIGS. 1A and 2A, the lenses 110 can be positioned at least partially within the tube 125. The tube 125 can be made of many different materials, including metals, plastics, composites, and combinations thereof. The tube 125 can be either flexible or rigid. The tube can also be many different shapes. As shown in FIGS. 1A and 2A, the tube 125 can be an elongated cylinder, such that it may contain various components of the imaging system.

The endoscopic imaging system can further comprise a light source 120 configured to illuminate the point of interest. The light source can be many different light sources. In some embodiments, the light source 120 can comprise a plurality of optical fibers. The optical fibers can have a first end 121 positioned adjacent the first ends 111 of the lenses 110. Thus, light from the light source can be directed to the point of interest and be reflected back to the first ends 111 of the lenses.

In some embodiments, the endoscopic imaging system can further comprise a body configured to support the camera 105, the relay lens system 115, and the plurality of GRIN optical lenses 110. The body can comprise an aperture 130. The second ends 122 of the one or more optical fibers can be positioned adjacent the aperture 130, such that light from an area outside the body (e.g., ambient light or rays of light directed toward the aperture) can pass through the aperture 130, to the second ends 122 of the one or more optical fibers 120, out of the first ends 121 of the optical fibers 120, and to the point of interest.

The system can also comprise a process and a memory. In some embodiments, the processor and memory can be integrated with the camera 105. In other embodiments, the processor and memory can be independent of the camera 105. The memory can comprise instructions that, when executed by the processor, cause the processor to carry out various functions. For example, the processor can generate image data corresponding to the light received from each of the plurality of GRINs lenses 110. The processor can then deconvolve the image data to generate deconvolved image data representative of the distinct images of the distinct perspective views of the point of interest relative to the respective GRIN lenses. In some embodiments, deconvolving the image data can comprise applying a Richardson-Lucy deconvolution method to the image data (discussed in detail below). In some embodiments, deconvolving the image data can comprise applying a point spread function associated with the endoscopic imaging system to the image data. The processor can then use the deconvolved image data to generate 3D image data representative of a 3D image of the point of interest. The processor can also generate an output signal to a display to cause the display to display the 3D image of the point of interest.

The following examples further illustrate aspects of the present disclosure. However, they are in no way a limitation of the teachings or disclosure of the present disclosure as set forth herein.

EXAMPLES

Figure 3A:
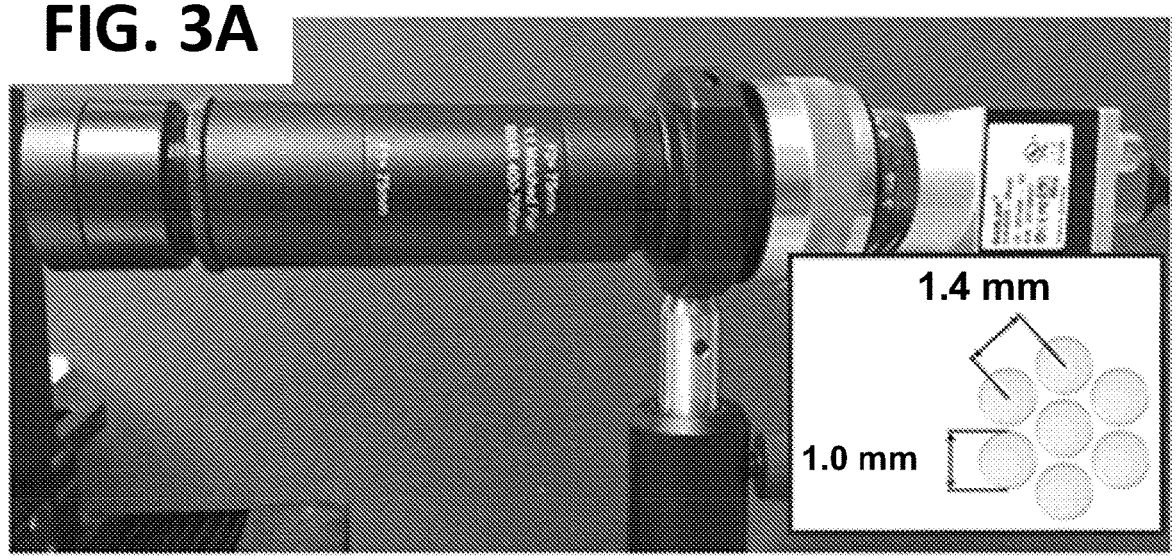
FIG. 3A and FIG. 3B provide a photograph and schematic of an endoscopic imaging system, in accordance with an embodiment of the disclosure.
Figure 3B:
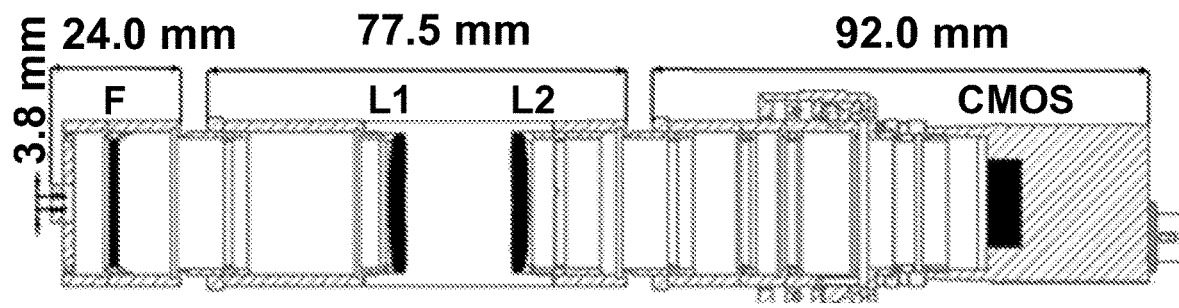

An endoscopic imaging system was constructed using an array of seven 1-mm, 0.5 NA GRIN lenses (GT-IFRL-100-005-50-CC, GRINTECH), as shown in FIGS. 3A-B. The GRIN lenses were arranged in a hexagonal array using a 3D-printed lens holder with 1.4-mm pitch and 3.8-mm overall diameter. The sample was placed in a six-axis kinematic optical mount (K6XS, Thorlabs) and positioned by two 1D translation stages (XR25C/M, Thorlabs) in the two lateral dimensions and a motorized 1D translation stage (NRT150/BSC201, Thorlabs) in the axial dimension. Transilluminated diffused white light from the sample was collected by the GLA and filtered by a bandpass filter (ET525/50, Chroma). The intermediate image was relayed with 1.5× magnification by a doublet lens (MAP107575-A, Thorlabs) and imaged onto a CMOS sensor (acA4024-29, Basler). It should be noted that the scope was contained and assembled using 1-inch threaded tubes (SM1, Thorlabs) primarily for the simplicity of instrumentation. In fact, the GLA at the entrance and the subsequent light propagation accommodate a substantially smaller dimension, allowing for feasible reduction of the prototype size to clinically preferred profiles.

Figure 3C:
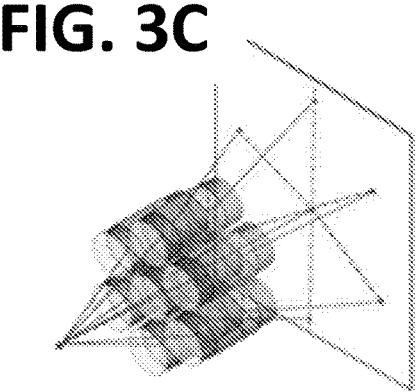
FIG. 3C illustrates image formation of a point source at an intermediate image plane of the system.
Figure 3D:
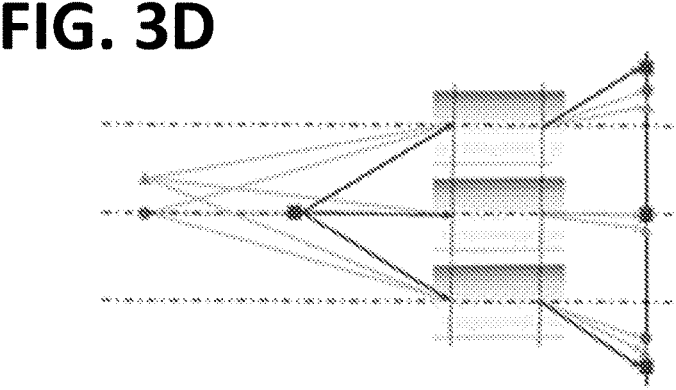
FIG. 3D provides an illustration of the image formation of point sources at varying lateral and axial positions, showing uncompromised recording of both the spatial and angular information.

The image formation in the light-field system is illustrated in FIGS. 3C-D. As seen, the light field from the sample is imaged by the GLA, forming individual depth-encoded perspective views in different regions on the camera. This scheme allows both the spatial and angular components to be recorded in an uncompromised and well-aliased manner. To reconstruct the volumetric information, a wave-optics based algorithm was implemented through PSF deconvolution, which is discussed in detail below. Using this wave-optics formulation, the algorithm considers the diffraction of light in the actual light-field system, which has largely been overlooked by ray optics, allowing for better spatial resolution and the recovery of finer spatial details.

The PSF of the light-field endoscopic system was acquired by axially scanning a transilluminated 25-µm pinhole (P25D, Thorlabs) along the central optical axis of the GLA. The PSF images were recorded across an axial range of 10.2 mm (i.e. 12.2 mm to 2 mm away from the GLA front surface) with a 50-µm step size for a total of 205 layers. It should be noted that the imperfections in the experimental PSF, e.g., the intensity variations in the signal or the background, may result in restrictive computational artifacts in the deconvolution. Therefore, a hybrid PSF strategy was derived by replacing the experimental PSF image at each layer with a simulated image of 2D Gaussian profile located at the same centroid. For optimum sampling based on the resolution of the system, the variation of these Gaussian profiles was chosen equal to 1.5× pixels (physical pixel size=1.85 µm) on the camera. Notably, such a hybrid PSF considers the actual experimental setting (e.g., misalignment, aberrations, etc.) that deviates from the theoretical description of light-field propagation, while rejecting many unnecessary sources of intensity variations that result in cumulative computational artifacts in the deconvolution iterations. Furthermore, we introduced two main calibration steps prior to reconstruction to address the image distortion and the depth-dependent magnification in the image formation of the GLA, which are discussed in detail below.

Figure 4A:
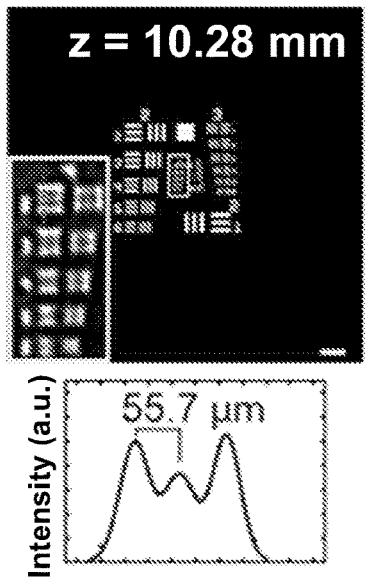
FIGS. 4A-G provide reconstructed images of a USAF target recorded at different axial depths from the GLA and cross-section profiles of the finest resolvable elements marked by the dotted lines and boxed regions at each depth.
Figure 4B:
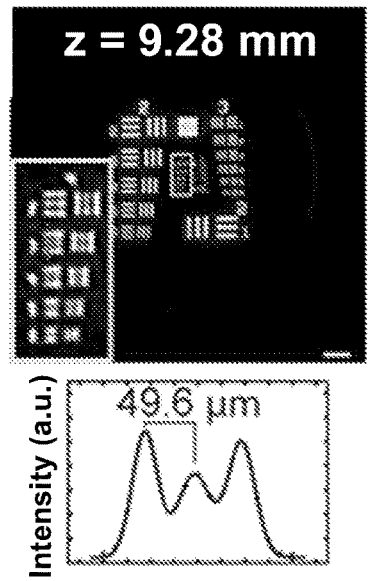
Figure 4C:
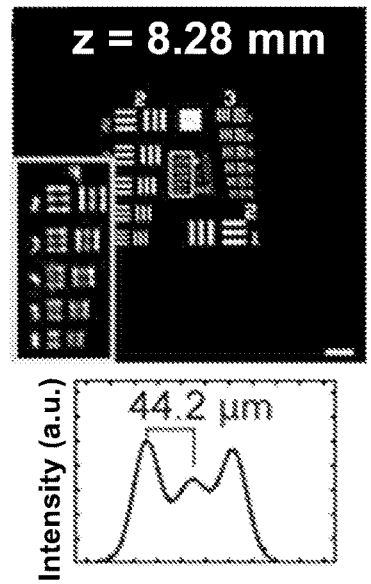
Figure 4D:
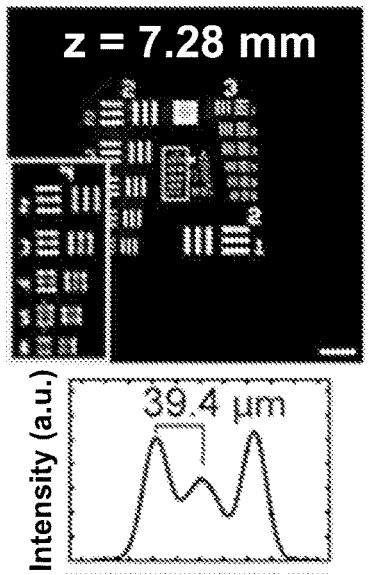
Figure 4E:
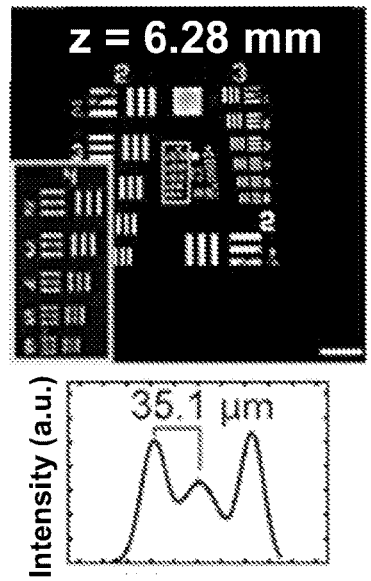
Figure 4F:
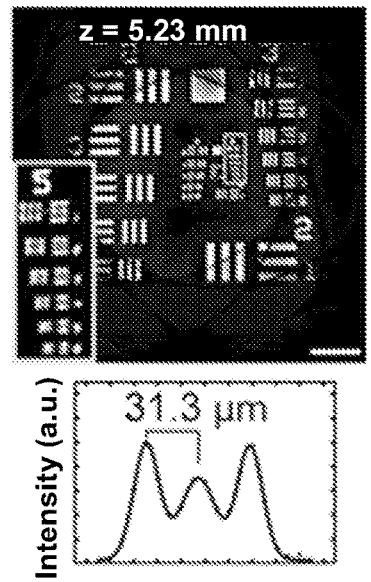
Figure 4G:
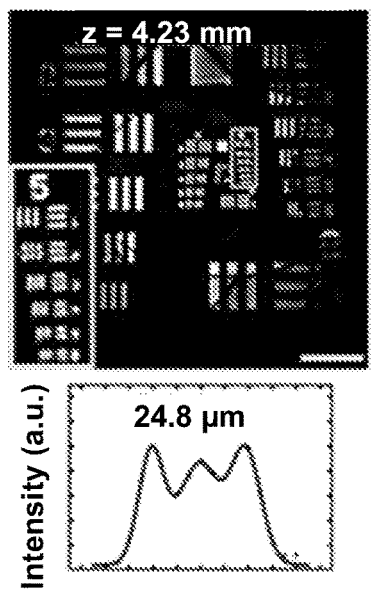
Figure 4H:
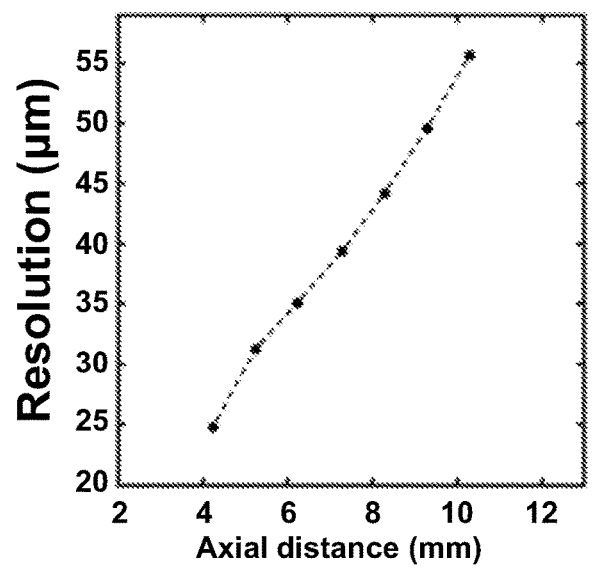
FIGS. 4H-J provide plots of measurements of the lateral resolution, FOV, and viewing angle as a function of the axial distance from the GLA.
Figure 4I:
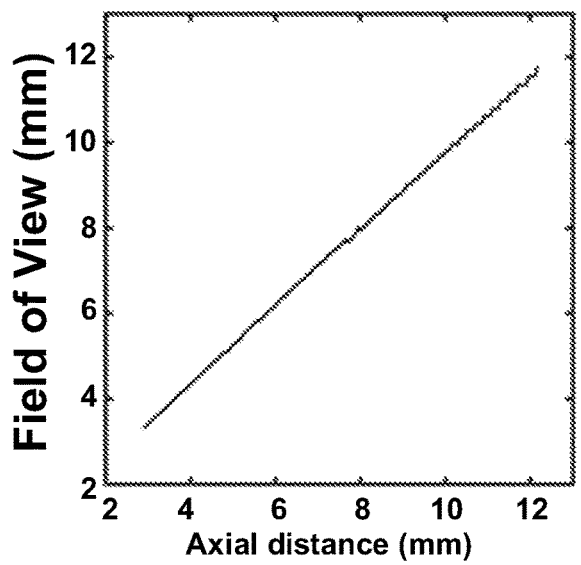
Figure 4J:
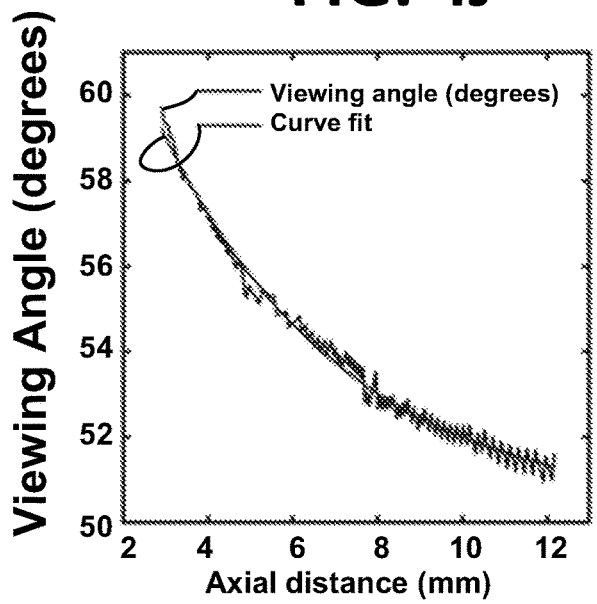

To test the performance of the endoscopic imaging system, a USAF resolution target (R1DS1N, Thorlabs), mounted perpendicular to the optical axis on a motorized translation stage was first imaged. The light-field images of the target were recorded and reconstructed at varying axial positions, and as observed, can be quantitatively recovered at depths across a >10-mm range at a lateral resolution of 20-60 μm without noticeable artifacts in the field of view (FOV), as shown in FIGS. 4A-G. In particular, as shown, when the object was positioned toward the GLA from z=10.28 mm to 4.23 mm, the magnification of the system increases. As a result, finer target structures of characteristic scales from 55.7 μm to 24.6 μm can be resolved, exhibiting a linear improvement of the resolution closer to the GLA, as shown in FIG. 4H. Meanwhile, as the magnification increases toward the GLA, the field of the object imaged in each individual perspective view is reduced, and accordingly, the effective imaging area contained in all these perspective images (i.e. the system FOV) decreases in a linear manner as measured in FIG. 4I. Outside of the system FOV, it is observed that the target can still be restored given a subset of the GLA images with a moderately compromised resolution, resulting from the reduced spatial and angular information (e.g., FIGS. 4F-G). It should also be noted that the visual consistency of the system is largely maintained, as the viewing angle, determined by the FOV and the corresponding depth, exhibits a gradual variation between 50°-60° over a >10-mm axial range, as shown in FIG. 4J.

Figure 5A:
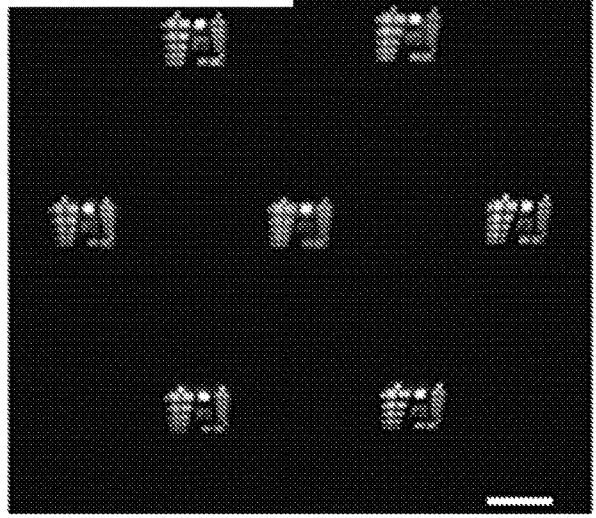
FIG. 5A provides raw field images of a USAF target inclined at 42 degrees.
Figure 5B:
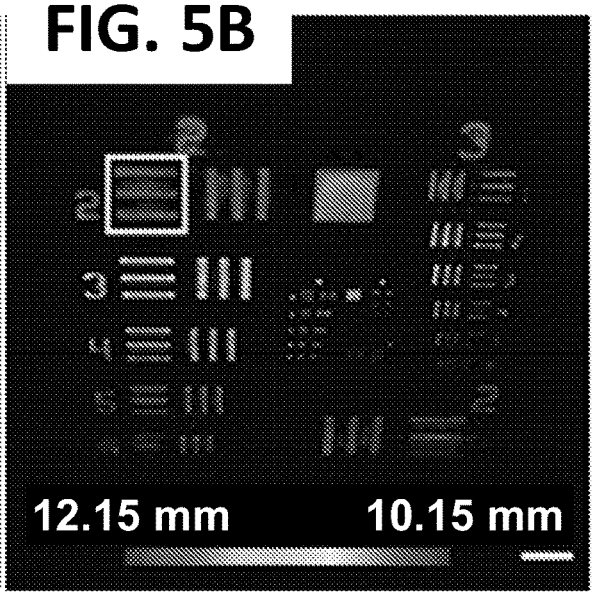
FIG. 5B provides the corresponding 3D reconstructed image.
Figure 5C:
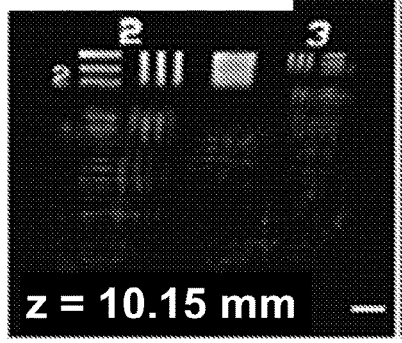
FIGS. 5C-E provide focal stacks of FIG. 5B at depths of 10.15 mm (FIG. 5C), 11.15 mm (FIG. 5D), and 12.15 mm (FIG. 5E) from the GLA.
Figure 5D:
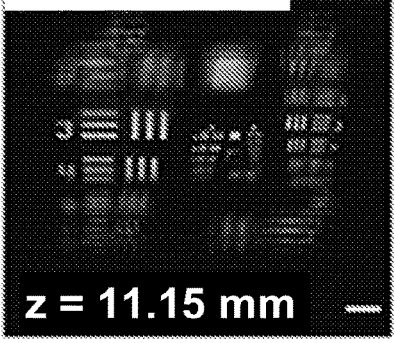
Figure 5E:
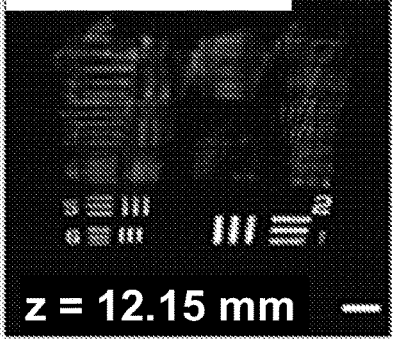

We next mounted the USAF target on a rotation stage (PR01, Thorlabs), tilted 42° towards the GLA with respect to the sample plane. As seen in FIG. 5A, the raw light-field data from a single camera frame contained different perspective views of the target. The corresponding region of interest, spanning a FOV of ~5 mm×5 mm and an axial range of 2-3 mm, can be reconstructed using the light-field information, allowing to synthesize the focal stacks of the target as shown in FIGS. 5B-E. As observed from the cropped region of Element 2 Group 2 of the USAF target, the reconstructed image stacks can clearly display the depth variations within each bar of a width of ~100 μm, as shown in FIGS. 5F-G. The surface information contained in these stacks was extracted by showing the weighted maximum intensity, as shown in FIG. 5H-I. The cross-sectional view of the reconstructed image exhibited a surface slope of 46°, consistent with the preset inclination. In addition, the axial projection of the surface information resolves the line pairs (i.e. 4.49 lp/mm as in Element 2 Group 2) separated by 136 μm and 105 μm in the axial dimension. Due to the discrete axial pixel size of 50 μm determined by the PSF, these values are within one pixel of the predicted value of 149 μm, implying an axial resolution between 100-200 μm.

Lastly, a transilluminated "Georgia Tech" logo placed on a hollow conical tube was imaged. A volumetric dataset spanning an entire FOV over >10 mm and a depth of several millimeters can be reconstructed from the raw data shown in FIG. 6A. The synthesized focal stacks allow visualization of optical signals originating from different depths. For example, the positional information of the letter "e" of "Georgia" and the letters "T" and "c" were fully recovered at z=12.75 mm and 11.4 mm, respectively, as shown in FIGS. 6B-C. Notably, the focal variations (or the axial sectioning capability) across a letter in each focal stack can be observed for structures located at different axial positions below 200 μm. A fine line pair separated by ~100 μm can be well resolved in the reconstructed image, as shown in FIG. 6D. Furthermore, the cross-sectional profiles of the 3D reconstructed logo agreed well with the actual profile of the curved surface, exhibiting a conical diameter of 27 mm, consistent with the actual 30-mm tube diameter, as shown in FIGS. 6E-F.

In summary, the 3D light-field endoscopic system allows for dense sampling of both the spatial and the angular information of optical signals through an array of GRIN lenses. Using the strategy combining wave-optics and the hybrid PSF, the system can quantitatively reconstruct the full volume from a single camera frame with a higher resolution in all three dimensions compared to the existing ray-optics and visual parallex methods. Experimentally, the system was validated with an imaging volume of >5 mm×5 mm×10 mm and a resolution of 20-60 μm and 100-200 μm in the lateral and axial dimensions, respectively. It should be noted that although the system was constructed using 1-inch lens tubes, the actual diameter of the GLA is <5 mm, thus implying a readily miniaturizable design, e.g. by adopting a Hopkin's relay system, longer endoscopy GRIN lenses, or customized optical elements. Combining such new optical instrumentation using clinically-relevant design parameters, as well as faster reconstruction algorithms, the system can achieve glasses-free, 3D human visual navigation into various complex microenvironments, offering a promising paradigm for 3D medical endoscopy.

Wave-Optics Based Algorithm

Mathematically, the reconstruction algorithm solves the inverse problem of recovering the radiant intensity at each point in the 3D object volume, denoted with v, given the captured camera image I. The two pieces of information satisfy the relationship I=Hv, where the measurement matrix H is determined by the PSF, expressed as $PSF(x'',p)=|h(x'',p)|^2$, $PSF(x'',p)=|h(x'',p)|^2$ where $x''(xx''=(x''_1,x''_2)Å\mathbb{R}^2$ represents the coordinates on the camera plane, and $p=(p_1,p_2,p_3)\in\mathbb{R}^3$ is the position for a point source in a volume in the object domain. The elements $h_{j,k}$ represent the projection of the optical signal at the pixel $I^{(j)}$ on the camera from the $k^{th}$ calculated voxel $v^{(k)}$ in the 3D object space. To obtain v, the inverse problem thus adopts Richardson-Lucy deconvolution $v^{(k+1)}=\text{diag}[\text{diag}(H^THv^{(k)})^{-1}(H^TI)]v^{(k)}$, where the operator diag{ } diagonalizes a matrix. The 3D deconvolution corresponds to taking forward projection ($Hv^{(k)}$) and backward projection ($H^TI$ and $H^THv^{(k)}$) iteratively between the 3D object space and the 2D image plane. Considering the spatial invariance in practice, the PSF can be described by an emitter located on the optical axis, i.e. p=(0,0,z). Therefore, the forward projection can be derived as a sum of 2D convolution layer by layer across the depth of focus of $[z_0, z_1]$, i.e. $Hv^{(k)}=\Sigma_{z=z_0}^{z=z_1}PSF(x'',z)\otimes v^{(k)}(z)$, where ⊗ is the convolution operator, and $v^{(k)}(z)$ represents the single layer of the 3D object located at the depth of z. Similarly, the back projection can thus be derived as $[H^TI](z)=PSF'(x'',z)\otimes I$ and $[H^THv^{(k)}](z)=PSF'(x'',z)\otimes Hv^{(k)}$, where PSF'(x'',z) is obtained by rotating PSF(x'',z) by 180 degrees.

Image Distortion

Compared to compound objective lenses, GRIN lenses usually suffer from severe optical aberrations, especially the characteristic barrel distortion that leads to a warped, non-uniform FOV in each individual image in the array, prohibiting reconstruction with a unified PSF. A caliber grid target was utilized to flatten and register all the channels, thus allowing for viable subsequent 3D reconstruction.

The barrel distortion created by a GRIN lens is related to its nonlinear refractive index profile, causing a warped field of view[3]. The classical correction model of barrel distortion is given as:

$$x_c(x_d,y_d)=x_d(1+k_1r_d^2+k_2r_d^4+\ldots), \text{ and}$$

$$y_c(y_d, y_d) = y_d(1 + k_1 r_d^2 + k_2 r_d^4 + \ldots).$$

where $r_d = \sqrt{x_d^2 + y_d^2}$ represents the radial distance from the center of the image to the original position $(x_d, y_d)$, and $(x_c, y_c)$ represents the corrected coordinates. An example of the original image and the corrected and condensed image are shown in FIGS. 7A-D.

Depth-Dependent Magnification

The magnification of the relay images exiting the GRIN lenses varies as a function of the depth of the object, leading to inconsistent voxel sizes, FOVs, and corresponding viewing angles across the reconstructed volume. Thus, the magnification of the system was calibrated across a >10-mm axial range, showing good agreement with the theoretical results and caliber structures.

Figure 8A:
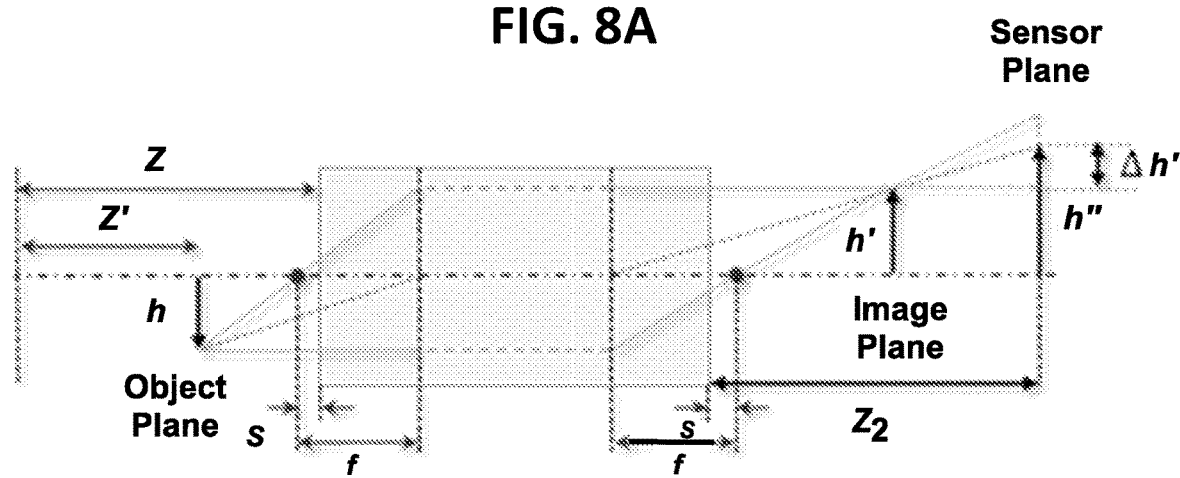
FIG. 8A provides a diagram of a GRIN lens where 0 is the end of the recorded PSF, Z is the distance between the end of the PSF and the GRIN lens, and z' is the distance from the end of the recorded PSF to the object (h) being imaged.

The parameters of the GRIN lens, i.e., the focal length f and the working distance s between the focal point and the entrance, as shown in FIG. 8A, can be determined as $$f = \frac{1}{n_0} \times \frac{1}{g \sin(gL)} = 0.8798 \text{ mm}; \quad s = \frac{1}{n_0} \times \frac{1}{g \tan(gL)} = -0.1419 \text{ mm}$$

(the focal point is located inside of the lens), where the length of the GRIN lens L=2.46 mm, $n_0$=1.635, and the scale factor $$g = \frac{\pi}{2 \times 2.23} \text{ mm}^{-1}.$$

Figure 9A:
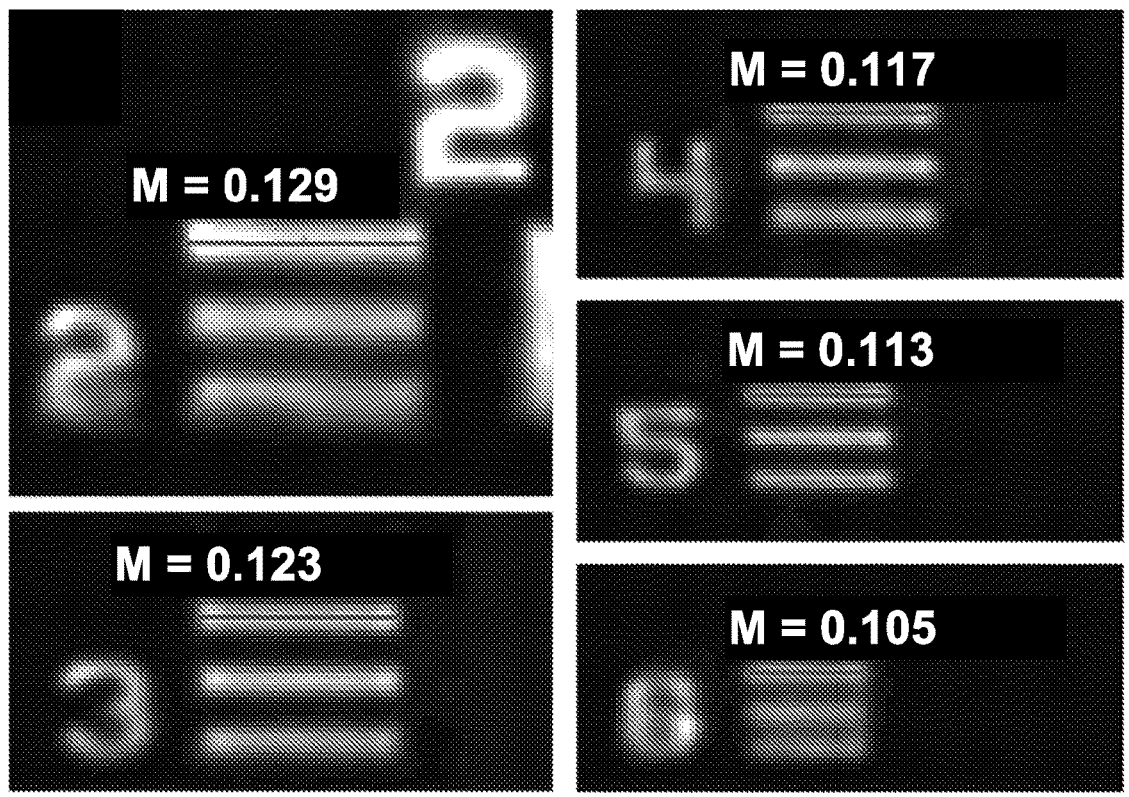
FIG. 9A provides reconstructed images of a tilted USAF target as shown in FIG. 5A at the depths of 12.15 mm, 11.9 mm, 11.4 mm, 10.75 mm, and 10.1 mm for Groups 2-6, respectively.
Figure 9B:
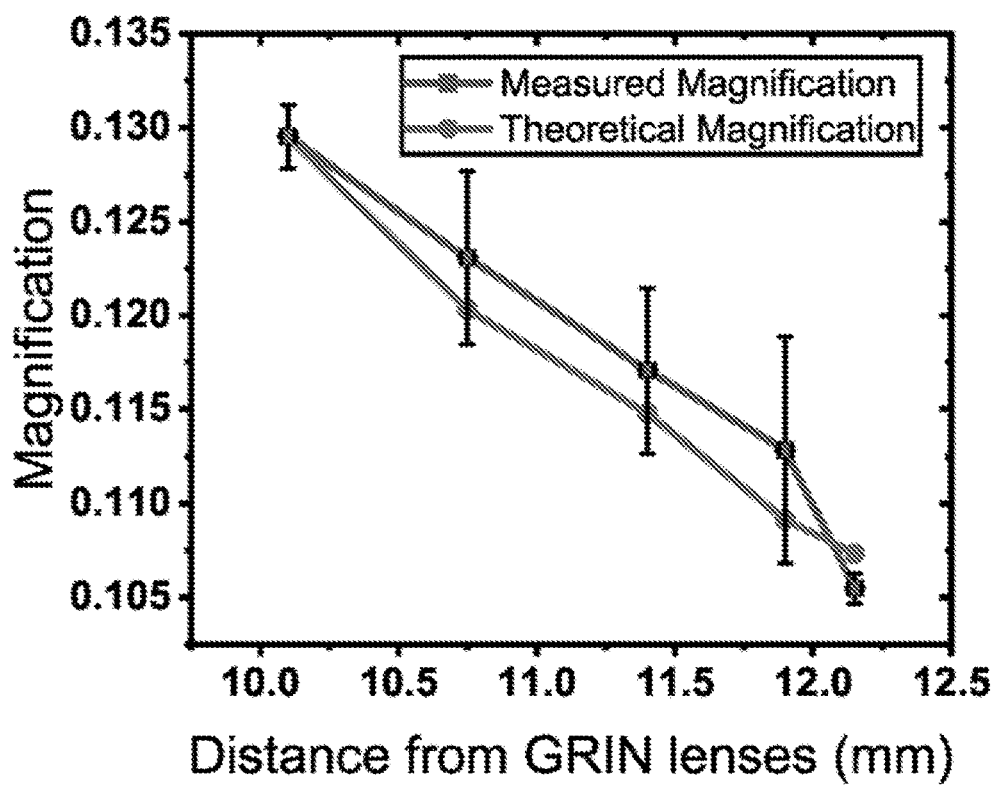
FIG. 9B provide plots of measured and theoretical depth-dependent magnification values.

Using ray optics shown in FIG. 8A, the magnification of the system can be derived as $$M_Z = \frac{1.5 h''}{h} = \frac{1.5(h' + \Delta h')}{h} = 1.5 \times M_1 \times \left(1 + \frac{z_2 - s - M_1 f}{f(M_1 + 1)}\right),$$

$$\text{where } M_1 = \frac{f}{Z - z' - s},$$

representing the magnification of the system on the image plane, and 1.5× represents the magnification introduced by the relay lenses. As seen, the magnification varies with the axial position along the z axis, increasing when the object is approaching the system, leading to inconsistent effective pixel size in the reconstructed 3D object layers, as shown in FIGS. 9A-B.

Figure 8B:
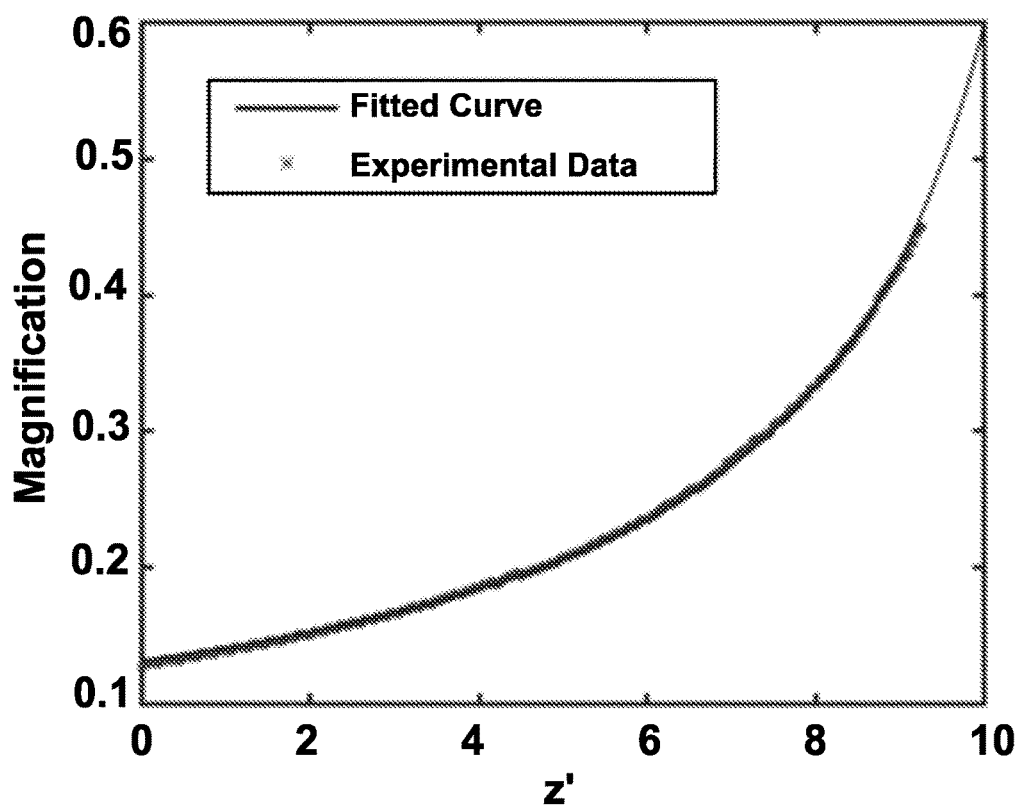
FIG. 8B provides experimentally measured and theoretical magnification as a function of axial positions. The theoretical curve uses the equation of M by fitting Z to the experimental data.

To generate the fitting curve in FIG. 8B, the MATLAB function fit( ) is adopted to fit the experimental data, using the target magnification function $$M_Z = 1.5 \times \frac{f}{a - z' - s} + b.$$

Based on the theoretical equation above, the variables a and b are determined by fitting the experimental data. In practice, a=12.16 and b=0.02511 were obtained. As shown in the experimental measurements, the magnification increases from 0.128 (z'=0 mm) to 0.363 (z'=8.4 mm), i.e., the pinhole is accordingly positioned from Z=12.16 mm to 3.76 mm away from the front surface of the GRIN lens array. The equivalent pixel size $p_Z$ along the z axis can thus be obtained by $$\frac{1.85 \mu m}{M_Z},$$

where 1.85 μm is the physical pixel size of the camera.

Another process to note is that the pixel size of each layer from Z=12.16 mm to 3.76 mm in the reconstructed volume was adjusted after 3D deconvolution, given the determined and interpreted magnification values from Z=12.16 mm to 3.76 mm with an axial step size of 50 μm. As the magnification increases towards the GRIN lens array, the reconstructed layer at Z=3.76 mm has the finest pixel size (denoted by $p_{REF}$), which can be used as a reference size. The magnification at this layer is represented by $M_{REF}$. Reconstructed layers subsequent along the z axis were then resized by the ratio $$\frac{p_z}{p_{REF}} \left(i.e. \frac{M_{REF}}{M_Z}\right),$$

using the MATLAB function imresize( ) where $p_Z$ is the pixel size of the reconstructed layer at the depth of Z. Lastly, all the layers with adjusted pixels are cropped into the same image size for consistence to form the final volumetric stacks.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. An endoscopic imaging system comprising:
   a camera;
   gradient-index (GRIN) optical lenses, each having:
      a first end configured to be inserted into a cavity of a subject and receive light reflected from a point of interest in the cavity of the patient; and
      a second end configured to transmit the light to the camera;
   a processor; and
   a memory comprising instructions that, when executed by the processor, cause the processor to:

generate image data corresponding to light received by the camera from the GRIN optical lenses, each respective GRIN optical lens providing a distinct perspective view of the point of interest;

deconvolve at least a portion of the image data to generate deconvolved image data representative of the distinct perspective views of the point of interest relative to the respective GRIN optical lens; and using at least a portion of the deconvolved image data, generate three-dimensional (3D) image data representative of a 3D image of the point of interest.

2. The endoscopic imaging system of claim 1 further comprising a relay lens system comprising one or more relay lenses;

wherein the relay lens system is configured to receive the light from the second ends of each GRIN optical lens and transfer the light to the camera.

3. The endoscopic imaging system of claim 1, wherein the GRIN optical lenses are arranged substantially parallel to one another.

4. The endoscopic imaging system of claim 1 further comprising a tube;

wherein the GRIN optical lenses are located, at least partially, within the tube.

5. The endoscopic imaging system of claim 4, wherein the tube is in the shape an of elongated cylinder.

6. An endoscopic imaging system comprising:
a camera;
three or more gradient-index (GRIN) optical lenses, wherein each respective GRIN optical lens:
has a first end configured to be inserted into a cavity of a subject and receive light reflected from a point of interest in the cavity of the patient; and
has a second end configured to transmit the light to the camera;
a processor; and
a memory comprising instructions that, when executed by the processor, cause the processor to:
generate image data corresponding to light received by the camera from each respective GRIN optical lens, wherein the light received from each respective GRIN optical lens is representative of a distinct image of a distinct perspective view of the point of interest relative to the respective GRIN optical lens;
deconvolve at least a portion of the image data to generate deconvolved image data representative of the distinct images of the distinct perspective views of the point of interest relative to the respective GRIN optical lens; and
using at least a portion of the deconvolved image data, generate three-dimensional (3D) image data representative of a 3D image of the point of interest.

7. The endoscopic imaging system of claim 6, wherein the GRIN optical lenses are arranged such that a cross-section along a length of the lenses forms a triangular shape.

8. The endoscopic imaging system of claim 6, wherein the three or more GRIN optical lenses comprise seven GRIN optical lenses.

9. The endoscopic imaging system of claim 8, wherein the GRIN optical lenses are arranged such that a cross-section along a length of the lenses forms a hexagonal shape.

10. The endoscopic imaging system of claim 6 further comprising a light source configured to illuminate the point of interest.

11. The endoscopic imaging system of claim 10, wherein the light source comprises one or more optical fibers.

12. The endoscopic imaging system of claim 11, wherein one or more of the optical fibers comprises a first end positioned adjacent the first end of one of the GRIN optical lenses.

13. The endoscopic imaging system of claim 11 further comprising a body configured to support the camera and the GRIN optical lenses;

wherein each of the one or more optical fibers comprises a first end and a second end;
wherein each first end of the one or more optical fibers is positioned adjacent one or more of the first ends of the GRIN optical lenses;
wherein the body comprising an aperture; and
wherein each second end of the one or more optical fibers is positioned adjacent the aperture, such that light from an area outside the body can pass through the aperture to the second ends of the one or more optical fibers.

14. The endoscopic imaging system of claim 6, wherein the memory further comprises instructions, that when executed by the processor, cause the processor to generate an output signal to a display to cause the display to display the 3D image of the point of interest.

15. The endoscopic imaging system of claim 6, wherein the memory further comprises instructions, that when executed by the processor, cause the processor to deconvolve the at least a portion of the image data to generate deconvolved image data by applying a Richardson-Lucy deconvolution method.

16. The endoscopic imaging system of claim 6, wherein the memory further comprises instructions, that when executed by the processor, cause the processor to deconvolve the at least a portion of the image data to generate deconvolved image data by applying a point spread function associated with the endoscopic imaging system.

17. A method of generating a three-dimensional (3D) image of a point of interest in a subject comprising:
inserting first ends of gradient-index (GRIN) optical lenses into the subject;
receiving, with each of the first ends of the GRIN optical lenses, light reflected from the point of interest, the light representative of a distinct image of a distinct perspective view of the point of interest relative to each respective GRIN optical lens;
transmitting the received light from second ends of the GRIN optical lenses to a camera;
generating image data corresponding to the transmitted light;
deconvolving the image data to generate deconvolved image data representative of the distinct images of the distinct perspective views of the point of interest relative to each respective GRIN optical lens; and
generating, using the deconvolved image data, 3D image data representative of a 3D image of the point of interest.

18. The method of claim 17 further comprising illuminating the point of interest;

wherein transmitting the received light from the second ends of the GRIN optical lenses to the camera comprises transmitting the received light from the second ends of the GRIN optical lenses through a relay lens system comprising one or more relay lenses and to the camera.

19. The method of claim 17, wherein the GRIN optical lenses are arranged substantially parallel to one another.

20. The method of claim 17, wherein the GRIN optical lenses are located, at least partially, within a tube; and wherein inserting the first ends of the GRIN optical lenses into the subject comprises inserting at least a portion of the tube into the subject.

21. The method of claim 20, wherein the tube is in the shape an of elongated cylinder.

22. The method of claim 17, wherein the number of GRIN optical lenses is selected from the group consisting of three and seven;
wherein the three GRIN optical lenses are arranged such that a cross-section along a length of the lenses forms a triangular shape; and
wherein the seven GRIN optical lenses are arranged such that a cross-section along a length of the lenses forms a hexagonal shape.

23. The method of claim 17 further comprising illuminating the point of interest with a light source comprising one or more optical fibers.

24. The method of claim 23, wherein each of the one or more optical fibers comprises a first end and a second end, the each first end of the one or more optical fibers is positioned adjacent the first ends of the GRIN optical lenses.

25. The method of claim 17 further comprising generating an output signal to a display configured to display the 3D image of the point of interest.

26. The method of claim 17, wherein deconvolving the image data to generate deconvolved image data comprises performing a Richardson-Lucy deconvolution method on the image data.

27. The method of claim 17, wherein generating the deconvolved image data comprises applying a point spread function associated with the endoscopic imaging system.

* * * * *